United States Patent
Lee (10) Patent No.: US 11,474,682 B2
(45) Date of Patent: Oct. 18, 2022

(54) CONTROL METHOD AND CONTROL DEVICE FOR AROMA DIFFUSER, MOBILE TERMINAL, AND STORAGE MEDIUM

(71) Applicant: Puzhen Life Co., Ltd., Shatin (HK)

(72) Inventor: Andy Lee, Shatin (HK)

(73) Assignee: PUZHEN LIFE CO., LTD., Shatin (HK)

( * ) Notice: Subject to any disclaimer, the term of this patent is extended or adjusted under 35 U.S.C. 154(b) by 0 days.

(21) Appl. No.: 17/387,653

(22) Filed: Jul. 28, 2021

(65) Prior Publication Data

US 2022/0276772 A1 Sep. 1, 2022

(30) Foreign Application Priority Data

Jan. 22, 2021 (CN) .......................... 202110090375.1

(51) Int. Cl.
| | |
|---|---|
| G06F 3/048 | (2013.01) |
| G06F 3/04847 | (2022.01) |
| G06F 3/16 | (2006.01) |
| A61L 9/14 | (2006.01) |
| H05B 45/20 | (2020.01) |
| G05B 13/02 | (2006.01) |
| H05B 45/10 | (2020.01) |

(52) U.S. Cl.
CPC ............ G06F 3/04847 (2013.01); A61L 9/14 (2013.01); G05B 13/0205 (2013.01); G06F 3/165 (2013.01); H05B 45/10 (2020.01); H05B 45/20 (2020.01); *A61L 2209/11* (2013.01)

(58) Field of Classification Search
None
See application file for complete search history.

(56) References Cited

U.S. PATENT DOCUMENTS

| | | | |
|---|---|---|---|
| 9,517,286 B1* | 12/2016 | Li ......................... | A61L 9/145 |
| 2011/0055720 A1 | 3/2011 | Potter et al. | |
| 2015/0358043 A1* | 12/2015 | Jeong ................... | H04B 1/385 455/411 |
| 2016/0012747 A1* | 1/2016 | Garrues Remirez .. | G09B 19/00 434/236 |
| 2018/0338241 A1* | 11/2018 | Li ......................... | G08B 5/222 |

(Continued)

FOREIGN PATENT DOCUMENTS

| | | | |
|---|---|---|---|
| CN | 105661854 A | 6/2016 | |
| CN | 108476232 A | 8/2018 | |

(Continued)

*Primary Examiner* — Tuan S Nguyen
(74) *Attorney, Agent, or Firm* — Cantor Colburn LLP (57) ABSTRACT

The present application relates to the technical field of an aroma diffuser, and more particularly to a control method and a control device for an aroma diffuser, a mobile terminal, and a storage medium. The control method includes: displaying an aroma diffuser control page, in which, the aroma diffuser control page includes a result reflection graph and at least one adjusting control; and adjusting, when an operation of the at least one adjusting control is detected, a working mode of the aroma diffuser, and updating a result reflection graph, in which, the result reflection graph shows an adjustment result of the working mode. Therefore, the aroma diffuser can be easily controlled, and the control result of the aroma diffuser can be presented on the result reflection graph.

12 Claims, 6 Drawing Sheets

(56) References Cited

U.S. PATENT DOCUMENTS

2018/0367330 A1   12/2018  Kang et al.
2020/0379730 A1*  12/2020  Graham ................. G06F 3/167
2021/0029795 A1*   1/2021  Chaturvedi ............ H05B 45/20

FOREIGN PATENT DOCUMENTS

| CN | 109491279 A | 3/2019 |
| CN | 109587908 A | 4/2019 |
| CN | 110568987 A | 12/2019 |

* cited by examiner

CONTROL METHOD AND CONTROL DEVICE FOR AROMA DIFFUSER, MOBILE TERMINAL, AND STORAGE MEDIUM

CROSS-REFERENCE TO RELATED APPLICATIONS

Pursuant to 35 U.S.C. § 119 and the Paris Convention Treaty, this application claims the benefit of Chinese Patent Application No. 202110090375.1 filed Jan. 22, 2021, the contents of which are incorporated herein by reference.

BACKGROUND

Technical Field

The present application relates to the technical field of an aroma diffuser, and more particularly to a control method and a control device for an aroma diffuser, a mobile terminal, and a storage medium.

Description of the Related Art

An aroma diffuser is a device that decomposes plant essential oils into a nano-scale cold mist that is easily absorbed by the human body, through the high-frequency oscillation generated by the ultrasonic vibration equipment or the high-speed gas generated by the air pump, and disperses the nano-scale cold mist in the surrounding air, making the air full of fragrance. The aroma diffuser has been widely used in homes, hotel rooms, lobbies, aisles, and other places.

In the related technology, the control of the aroma diffuser is usually realized by manually operating the buttons on the aroma diffuser, which is relatively inconvenient.

SUMMARY

The embodiment of the present application provides a control method, control device, mobile terminal and storage medium of the aroma diffuser, so as to control the aroma diffuser more simply, and display the control result of the aroma diffuser through the result reflection chart.

In a first aspect, an embodiment of the present application provides a control method for an aroma diffuser. The control method comprises:

displaying an aroma diffuser control page, in which, the aroma diffuser control page comprises a result reflection graph and at least one adjusting control;

adjusting, when an operation of the at least one adjusting control is detected, a working mode of the aroma diffuser, and updating a result reflection graph, in which, the result reflection graph shows an adjustment result of the working mode.

In a second aspect, an embodiment of the present application provides a control device for an aroma diffuser. The control device comprises:

a page display module, configured for displaying an aroma diffuser control page, in which, the aroma diffuser control page comprises a result reflection graph and at least one adjusting control; and an aroma diffuser control module, configured for adjusting, when an operation of the at least one adjusting control is detected, a working mode of the aroma diffuser, and updating a result reflection graph, in which, the result reflection graph shows an adjustment result of the working mode.

In a third aspect, an embodiment of the present application provides a mobile terminal. The mobile terminal comprises: a memory, a processor, and a computer program stored in the memory and running on the processor, in which, the processor is configured for realizing the steps of the control method according to the first aspect when executing the computer program.

In a fourth aspect, an embodiment of the present application provides a computer-readable storage medium storing a computer program, in which, the computer program is configured for implementing the steps of the control method according to the first aspect when the computer program is executed by a processor.

In a fifth aspect, an embodiment of the present application provides a computer program product, when running on a mobile terminal, the computer program product enables the mobile terminal executes the steps of the control method according to the first aspect.

Advantages of the present application are summarized as follows: in the embodiments of the present application, the aroma diffuser control page is displayed, and when the operation on the adjusting controls in the aroma diffuser control page is detected, the working mode of the aroma diffuser is adjusted. This process does not need to manually operate the button on the aroma diffuser, thereby being able to more conveniently realize the control of the aroma diffuser. In addition, the updating of the result reflection graph is able to display the adjustment result of the working mode of the aroma diffuser (that is, the control result of the aroma diffuser), thus being convenient for the user to observe the control result of the aroma diffuser more intuitively.

BRIEF DESCRIPTION OF THE DRAWINGS

In order to more clearly illustrate the technical solutions in the embodiments of the present application, the drawings that need to be used in the description of the embodiments or the prior art will be briefly described hereinbelow. Obviously, the accompanying drawings in the following description are only some embodiments of the present application. For those skilled in the art, other drawings can be obtained based on these drawings without creative work.

DETAILED DESCRIPTION OF THE EMBODIMENTS

In the following description, for the purpose of explanation rather than limitation, specific details are set forth such as particular system architectures, techniques, etc., in order to provide a thorough understanding of the embodiments of the present application. However, it will be apparent to those skilled in the art that the present application may be implemented in other embodiments that are not particularly subject to these specific details. In other instances, detailed descriptions of well-known systems, devices, circuits, and methods are omitted so as not to obscure the description of the present application with unnecessary detail.

It will be understood that the term "comprising"/"including", when used in this specification and the appended claims, represents the presence of stated features, integers, steps, operations, elements, and/or components, but does not preclude the presence or addition of one or more other features, integers, steps, operations, elements, components, and/or combinations thereof.

It is also to be understood that the terminology used herein in the specification of the present application is for the purpose of merely describing particular embodiments and is not intended to limit the present application. As used in the specification of the present application and the appended claims, unless otherwise clearly indicated in the context, the singular forms such as "a", "an" and "the" are intended to include the plural forms.

In specific implementations, mobile terminals described in embodiments of the present application include, but not limited to, other portable devices such as mobile phones, laptop computers, or tablet computers with touch-sensitive surfaces (for example, a touch screen display and/or a touch pad). It should be understood that in some embodiments, the device is not a portable communication device, but a desktop computer with a touch-sensitive surface (for example, a touch screen display and/or a touch pad).

In the following discussion, a mobile terminal including a display and a touch-sensitive surface is described. However, it should be understood that the mobile terminal may include one or more other physical user interface devices such as a physical keyboard, mouse, and/or joystick.

The mobile terminal supports various applications, such as one or more of the following: a drawing application, a presentation application, a word processing application, a website creation application, a disk burning application, a spreadsheet application, a game application, a phone Apps, a video conferencing apps, an email apps, an instant messaging application, an exercise support application, a photo management application, a digital camera application, a digital camera application, a web browsing application, a digital music player application, and/or a digital video player application.

Various applications that can be executed on the mobile terminal can adopt at least one common physical user interface device such as a touch-sensitive surface. One or more functions of the touch-sensitive surface and corresponding information displayed on the terminal can be adjusted and/or changed between applications and/or within corresponding applications. In this way, the common physical architecture of the terminal (for example, a touch-sensitive surface) can support various applications with a user interface that is intuitive and transparent to the user.

It should be understood that the magnitude of the sequence number of each step in this embodiment does not mean the order of execution, and the execution order of each step should be determined by its function and internal logic, and should not constitute any limitation on the implementation process of the embodiment of this application.

In order to illustrate the technical solution described in the present application, the technical solution of the present application is described hereinbelow by specific embodiments.

Figure 1:
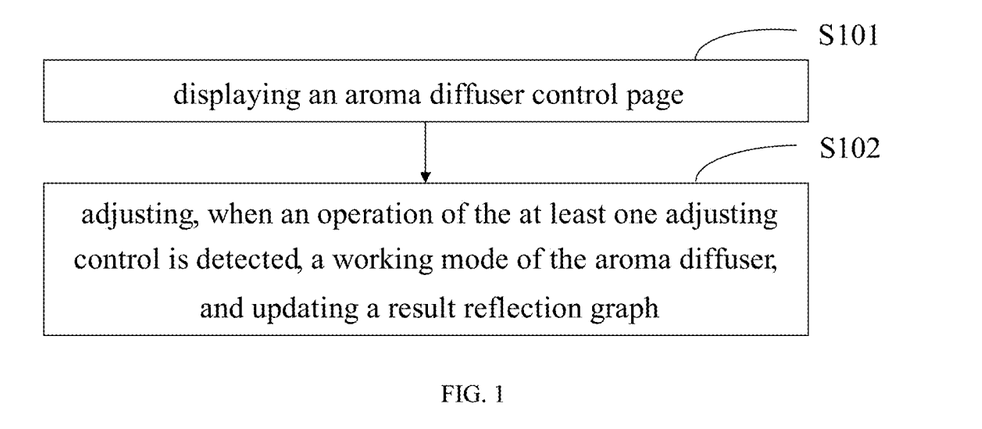
FIG. 1 is a flow chart of implementing a control method for an aroma diffuser provided by a first embodiment of the present application.

FIG. 1 is a flow chart of implementing a control method for an aroma diffuser provided by a first embodiment of the present application. The control method is applied to a mobile terminal. As shown in FIG. 1, the control method comprises the following steps:

Step 101 of displaying an aroma diffuser control page.

The aroma diffuser control page comprises a result reflection graph and at least one adjusting control. The at least one adjusting control is configured to adjust a working mode of the aroma diffuser. The result reflection graph shows an adjustment result of the working mode of the aroma diffuser. The adjustment result of the working mode of the aroma diffuser can be understood as the control result of the aroma diffuser. The type of the adjusting control may be a button, an edit boxes, and a toggle bar, which are not limited herein.

In this embodiment, an aroma diffuser control application program can be installed on the mobile terminal, and when a touch operation on an icon of the aroma diffuser control application program on a screen of the mobile terminal is detected, the aroma diffuser control application program is started, an interface for the aroma diffuser control application program is displayed on the screen of the mobile terminal, and the aroma diffuser control page is displayed on the interface for the aroma diffuser control application program. The aroma diffuser control application program refers to software that implements the control method for an aroma diffuser of the present application. The aforementioned touch operations include, but are not limited to, operations including single-click, double-click, and slide.

Before displaying the aroma diffuser control page, it is required to establish communication connection between the mobile terminal and the aroma diffuser. After the mobile terminal has successfully established a communication connection with the aroma diffuser, the aroma diffuser control application program can be started, and the aroma diffuser control page is displayed once the aroma diffuser control application program has been successfully started. It should be noted that an aroma diffuser control application program can correspond to one kind of aroma diffuser or at least two kinds of aroma diffusers, which is not limited herein. The connection between the mobile terminal and the aroma diffuser includes, but not limited to, a Bluetooth, a wireless fidelity (WiFi), a 3rd-generation mobile communication technology (3G), a 4th-generation mobile communication technology (4th-Generation, 4G), and a fifth-generation mobile communication technology (5th-Generation, 5G), etc.

Step 102 of adjusting, when an operation of the at least one adjusting control is detected, a working mode of the aroma diffuser, and updating a result reflection graph;

in which, the result reflection graph shows an adjustment result of the working mode.

When the operation of the at least one adjusting control is detected by the mobile terminal, the corresponding adjustment command can be generated and sent to the aroma diffuser by the mobile terminal. After the adjustment command is received by the aroma diffuser, the working mode of the aroma diffuser is adjusted according to the adjustment command.

Specifically, when the mobile terminal detects the operation of the at least one adjusting control, the mobile terminal can determine the working parameters of the aroma diffuser according to the operation of the adjusting control, generate an adjustment command including the above working parameters, and send the above adjustment command to the aroma diffuser. The aroma diffuser, upon receiving the above adjustment command, adjusts the working mode thereof according to the working parameters included in the above adjustment command. The above working parameters include, but are not limited to, an atomization amount, a total atomization duration, a brightness of a light source, a color of the light source, and so on. The above-mentioned atomization amount can also be referred to as an amount of a fog. The above-mentioned light source may refer to a Red-Green-Blue (RGB) three-color light emitting diode (LED) lamp. The color of the RGB three-color LED lamp can be adjusted or regulated by the processor in the aroma diffuser. The working mode of the above aroma diffuser can refer to a mode that instructs the aroma diffuser the mode of how to work and how to operate. For example, in the working mode, the atomization amount of the aroma diffuser is 350 mL/hr, the total atomization duration is 4 hrs, the brightness of the light source is 50 lux, and the color of the light source is red.

Figure 2A:
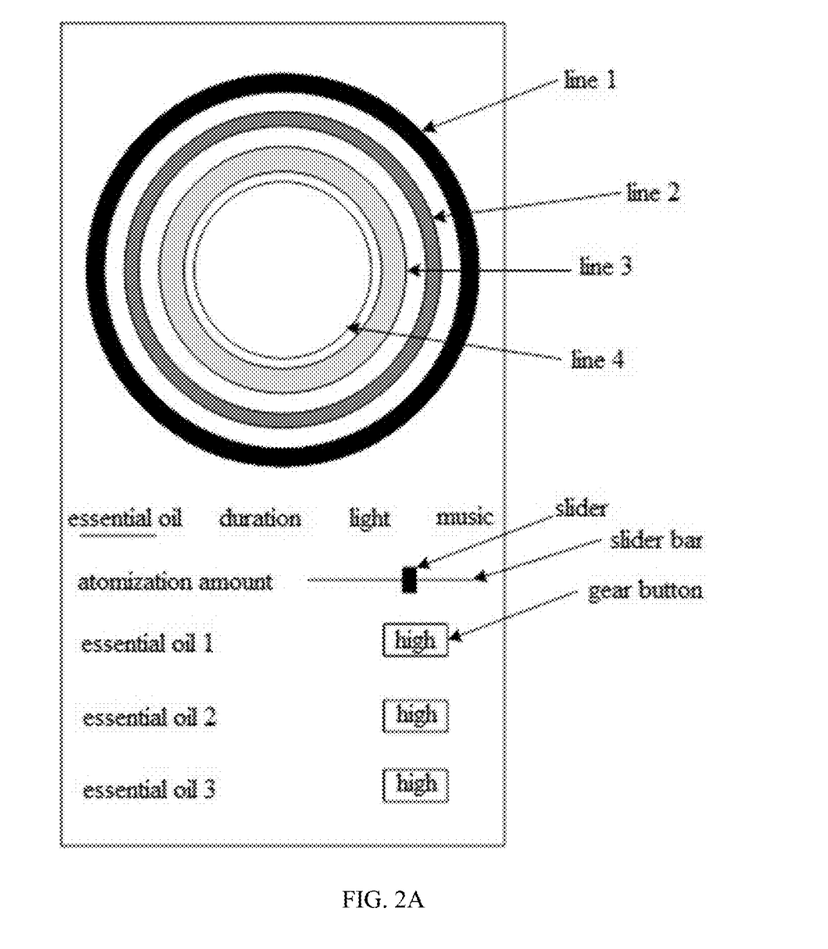
FIG. 2A is an exemplary image showing updating of an atomization amount reflection graph.

Optionally, the aroma diffuser is configured to store N essential oils, in which, N is an integer greater than zero. The aroma diffuser control page comprises an essential oil atomization control page, and the essential oil atomization control page comprises: a first adjusting control, and second adjusting controls respectively corresponding to the N essential oils. The result reflection graph comprises an atomization amount reflection graph. The atomization amount reflection graph comprises graph regions corresponding to the N essential oils respectively. The step of adjusting, when an operation of the at least one adjusting control is detected, a working mode of the aroma diffuser, and updating a result reflection graph comprises:

determining a first target atomization amount when an operation of the first adjusting control is detected;

adjusting atomization amounts of the N essential oils to the first target atomization amount, and updating graph regions corresponding to the N essential oils respectively;

determining one or more second target atomization amounts when an operation of one or more of the second adjusting controls is detected; and adjusting atomization amounts of one or more of the N essential oils corresponding to the one or more of the second adjusting controls to the one or more second target atomization amounts, respectively, and updating graph regions corresponding to the one or more types of the N essential oils, respectively.

N essential oil bins are provided in the aroma diffuser, each essential oil bin is configured to store one type of essential oil, and the N essential oil bins store N essential oils.

In one embodiment, the aroma diffuser control page may also include a scanning control and an essential oil name display region. The mobile terminal can scan an identification information of the N essential oils through the scanning control, whereby obtaining an essential oil name or an essential oil picture of the N essential oils. In the essential oil name display region, the respective essential oil name or the essential oil picture of the N essential oils are displayed, and the respective graph regions corresponding to the N essential oils are divided in the atomization amount reflection graph. The identification information may be a two-dimensional code, a barcode, etc., containing the essential oil name or the essential oil picture. The essential oil picture may refer to a picture including an essential oil label or an outline of an essential oil bottle.

When the operation on the first adjusting control is detected, the first target atomization amount can be determined according to the operation on the first adjusting control. For example, the first adjusting control is a gear slide bar. The gear slide bar includes a slide bar and a slider. When a sliding operation on the slider is detected, a position of the slider on the slide bar is determined, and the first target atomization amount is determined according to the position of the slider on the slid bar. It should be noted that before determining the first target atomization amount, a correspondence relationship between the position and the atomization amount can be acquired firstly, and the correspondence relationship at least includes a mapping relationship between the position of the slider on the slider and the first target atomization amount. The correspondence relationship between the position and the atomization amount can be acquired from the aroma diffuser control application program, or the correspondence relationship between the position and the atomization amount can be acquired from other devices, which is not limited herein.

For an i-th essential oil, the i-th essential oil is any of the above-mentioned N essential oils. The i-th essential oil corresponds to an i-th graph region in the atomization amount reflection graph. The atomization amount of the i-th essential oil may be represented by the i-th graph region, and difference in the atomization amount of the i-th graph region corresponds to difference in the i-th graph region.

When the operation on the second adjusting control is detected, the second target atomization amount can be determined according to the operation on the second adjusting control. For example, the second adjusting control is a gear button, which corresponds to three atomization gears, that is, a high atomization gear, a medium atomization gear, and a low atomization gear. The high atomization gear is defined as a default gear. When the operation on the gear button is detected, the atomization gear is adjusted to the medium atomization gear, and the second target atomization amount is determined according to the medium atomization gear. It should be noted that before determining the second target atomization amount, the correspondence relationship between the atomization gear and the atomization amount needs to be acquired, and the correspondence relationship at least includes a mapping relationship between the medium atomization gear and the second target atomization amount. The correspondence relationship between the atomization gear and the atomization amount can be acquired from the aroma diffuser control application program, or the correspondence relationship between the atomization gear and the atomization amount can be acquired from other devices, which is not limited here.

As shown in FIG. 2A, which is an exemplary image showing updating of an atomization amount reflection graph, the aroma diffuser stores three essential oils, that is, an essential oil 1, an essential oil 2, and an essential oil 3. A circular region enclosed by a line 1 and a line 2 represents the graph region of the essential 1 in the atomization amount reflection graph; a circular region enclosed by the line 2 and a line 3 represents the graph region of the essential 2 in the atomization amount reflection graph; and a circular region enclosed by the line 3 and a line 4 represents the graph region of the essential 3 in the atomization amount reflection graph. Proportions of different colors in each circular region can be adopted to represent the atomization amount, for example, the greater the proportion of black in the circular region enclosed by the line 1 and the line 2 is, the greater the atomization amount is.

Figure 2B:
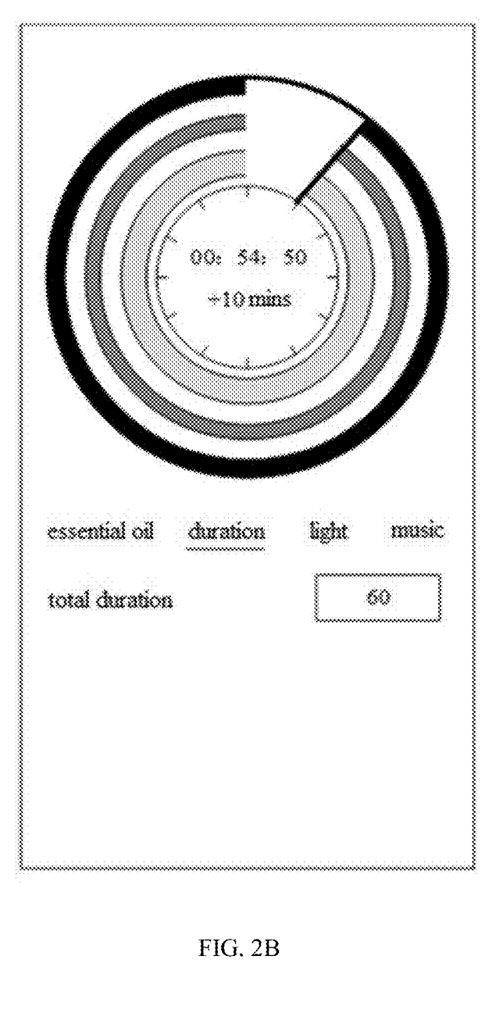
FIG. 2B is an exemplary image showing updating of an atomization duration reflection graph.

Optionally, the aroma diffuser control page comprises an atomization duration control page, and the atomization duration control page comprises a duration setting control and a duration adjusting control. The result reflection graph comprises an atomization duration reflection graph. The atomization duration reflection graph comprises a worked region and an un-worked region, in which, the worked region reflects an atomization duration that the aroma diffuser has been subjected, and the un-worked region reflects a remaining atomization duration of the aroma diffuser. The step of adjusting, when an operation of the at least one adjusting control is detected, a working mode of the aroma diffuser, and updating a result reflection graph comprises:

determining a total atomization duration when an operation of the duration setting control is detected;

adjusting an atomization duration of the aroma diffuser to be the total atomization duration, and displaying a countdown of the total atomization duration;

adjusting a proportion of the worked region and a proportion of the un-worked region in the atomization duration reflection graph according to the countdown; and adjusting the remaining atomization duration when an operation of the duration adjusting control is detected, and updating the countdown.

When the operation on the duration setting control is detected, the total atomization duration can be determined according to the operation on the duration setting control. For example, the duration setting control is an edit box, the total atomization duration can be input in the edit box, and the total atomization duration countdown can be displayed in the duration display region.

In order to distinguish the worked region and the un-worked region in the atomization duration reflection graph, the un-worked region can be displayed in a preset manner, such as updating the image of the un-worked region.

When the operation of the duration adjusting control is detected, the target duration can be determined according to the operation of the duration adjusting control, and the remaining atomization duration can be extended by the aforementioned target duration. For example, the duration adjusting control is a click button, and each time a click operation on the click button is detected, the remaining atomization time is extended by ten minutes.

As shown in FIG. 2B, which is an exemplary image showing updating of an atomization duration reflection graph, "60" is entered in the edit box corresponding to the total atomization duration to indicate that the total atomization duration is 60 minutes. In FIG. 2B, "+10 minutes" is the duration adjusting control, "00:54:50" represents the remaining atomization duration, and the worked region in the atomization duration reflection graph is updated to white color.

Optionally, the atomization duration control page further comprises a first duration control and a second duration control. The step of adjusting, when an operation of the at least one adjusting control is detected, a working mode of the aroma diffuser, and updating a result reflection graph further comprises:

determining an atomization opening duration of an intermittent cyclic atomization for the aroma diffuser when an operation of the first duration control is detected;

determining an atomization closing duration of the intermittent cyclic atomization for the aroma diffuser when an operation of the second duration control is detected; and controlling the aroma diffuser to perform the intermittent cyclic atomization according to the atomization opening duration, the atomization closing duration, and the total atomization duration, and re-dividing the worked region and the un-worked region in the atomization duration reflection graph.

When an operation on the first duration control is detected, the atomization opening duration can be determined according to the operation on the first duration control. For example, the first duration control is an edit box, and the atomization opening duration can be entered in the edit box.

When an operation on the second duration control is detected, the atomization closing duration may be determined according to the operation on the second duration control. For example, the second duration control is an edit box, and the atomization closing duration can be entered in the edit box.

When controlling the aroma diffuser to perform the intermittent cyclic atomization, within the total atomization duration, the atomization duration of the aroma diffuser may be firstly controlled to be the atomization opening duration, and then the aroma diffuser is controlled to stop the atomization for a duration as the atomization closing duration, after that, the atomization duration of the aroma diffuser is controlled to be the atomization opening duration again, in this way, the atomization cycle is performed until the remaining atomization duration is zero. For example, if the total atomization duration is 60 minutes, and the atomization opening duration and the atomization closing duration are both 10 seconds; the aroma diffuser is controlled to perform the atomization for 10 seconds, and then to stop the atomization for another 10 seconds, the atomization cycle is performed in this way for a total of 60 minutes.

Figure 2C:
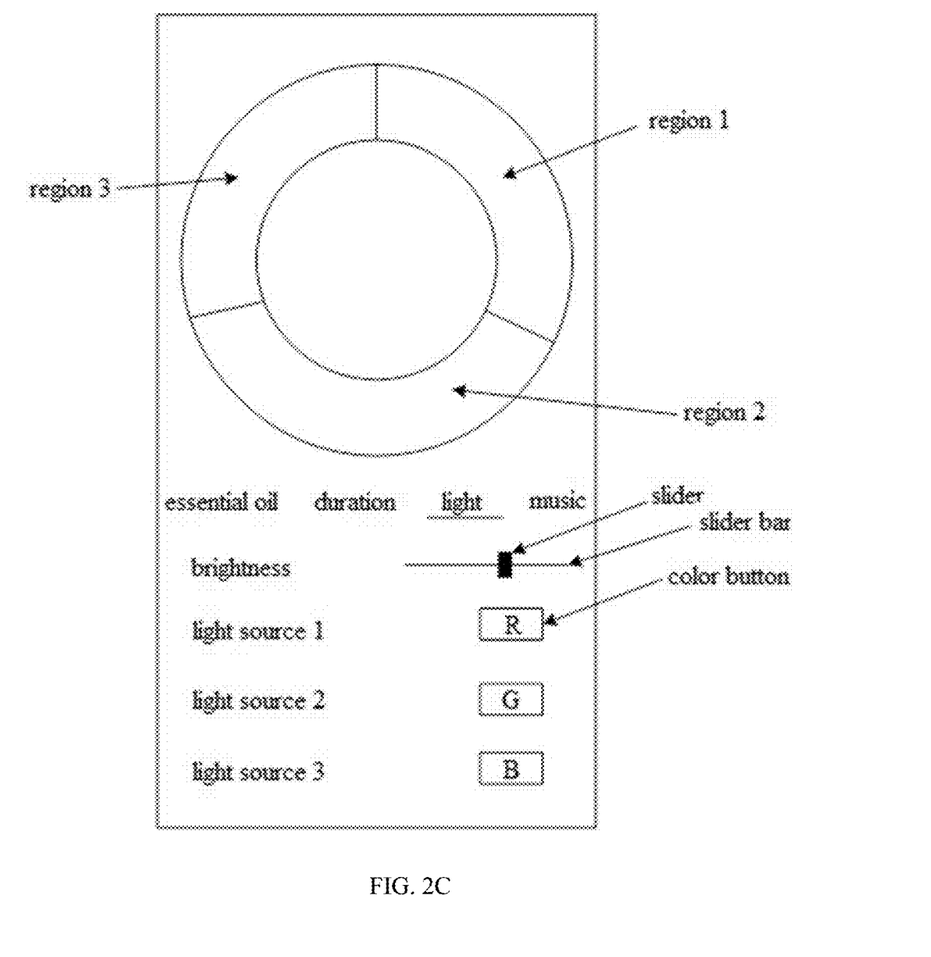
FIG. 2C is an exemplary image showing updating of a lighting state reflection graph.

Optionally, the aroma diffuser is provided with M light sources, where M is an integer greater than zero. The aroma diffuser control page comprises a lighting control page, and the lighting control page comprises: a brightness adjusting control, and color adjusting controls corresponding to the M light sources, respectively. The result reflection graph comprises a lighting state reflection graph, and the lighting state reflection graph comprises graph regions corresponding to the M light sources. The step of adjusting, when an operation of the at least one adjusting control is detected, a working mode of the aroma diffuser, and updating a result reflection graph comprises:

determining a target brightness when an operation of the brightness adjusting control is detected;

adjusting a brightness of the M light sources, and updating the brightness of graph regions corresponding to the M light sources respectively;

determining one or more target colors when an operation of one or more of the color adjusting controls is detected; and adjusting colors of one or more of the M light sources corresponding to the one or more of the color adjusting controls and colors of one or more of the graph regions corresponding to the one or more of the M light sources to the one or more target colors, respectively.

When the operation of the brightness adjusting control is detected, the target brightness can be determined according to the operation of the brightness adjusting control. For example, the brightness adjusting control is a brightness slider, the brightness slider includes a slider bar and a slider. When a sliding operation on the slider is detected, the position of the slider on the slider bar is determined, and the target brightness is determined according to the position of the slider on the slider bar. It should be noted that before determining the target brightness, a correspondence relationship between the position and the brightness may be acquired firstly, and the correspondence relationship at least includes a mapping relationship between the position of the slider on the slider bar and the target brightness. The correspondence relationship between the position and the brightness can be acquired from the aroma diffuser control application program, or the correspondence relationship between the position and the brightness can be acquired from other devices, which is not limited here.

For a j-th light source, the j-th light source is any of the above M light sources. The j-th light source corresponds to the j-th graph region in the lighting state reflection graph. The color of the j-th light source can be represented by the color of the j-th graph region.

As shown in FIG. 2C, which is an exemplary image showing updating of a lighting state reflection graph, the aroma diffuser is provided with three light sources, that is, a light source 1, a light source 2, and a light source 3. A region 1 represents a graph region corresponding to the light source 1 in the lighting state reflection graph, a region 2 represents a graph region corresponding to the light source 2 in the lighting state reflection graph, and a region 3 represents a graph region corresponding to the light source 3 in the lighting state reflection graph. The color of each graph region can be set to the light color of the light source corresponding to the graph region, such that the light color of the light source can be intuitively observed in the light state reflection graphs. The "R" (red), "G" (green), and "B" (blue) buttons in FIG. 2C are all color buttons. By clicking the color buttons, the light colors corresponding to the light sources and the colors of the graph regions corresponding to the light sources can be updated.

Figure 2D:
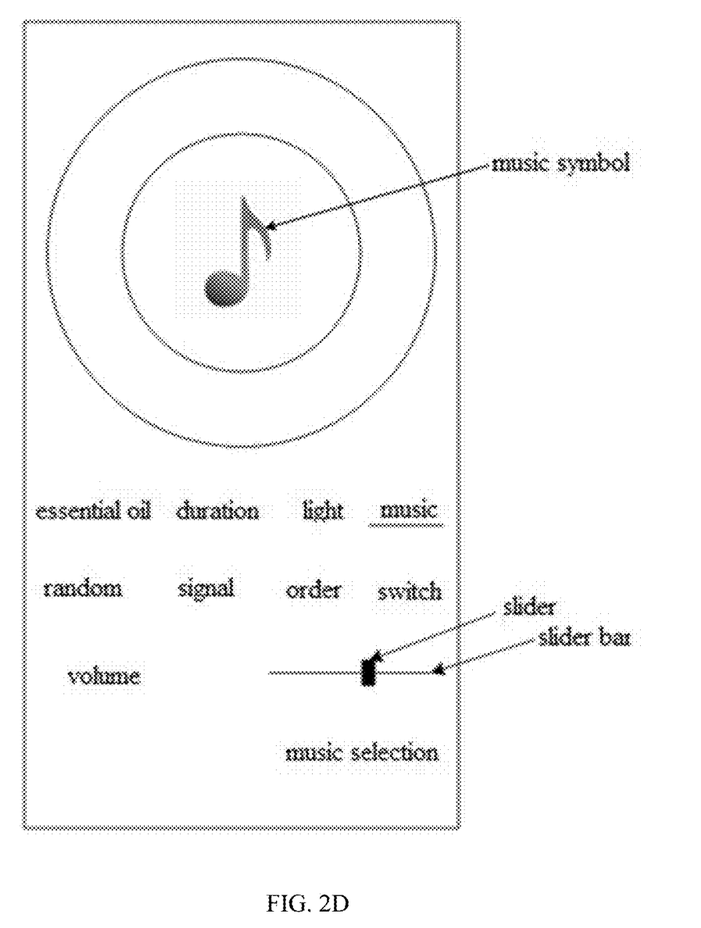
FIG. 2D is an exemplary image showing updating of the music switch reflection graph.

Optionally, the aroma diffuser control page comprises a music control page. The music control page comprises a switch control, and the result reflection graph comprises a music switch reflection graph. The step of adjusting, when an operation of the at least one adjusting control is detected, a working mode of the aroma diffuser, and updating a result reflection graph comprises:

controlling the aroma diffuser to play music or controlling the aroma diffuser to stop playing music, when an operation of the switch control is detected, and updating the music switch reflection graph;

in which, the music control page further comprises: a play adjusting control, a volume adjusting control, and a music selection control;

determining a target play mode when an operation of the play adjusting control is detected, and controlling the aroma diffuser to play music according to the target play mode;

determining a target volume when an operation of the volume adjusting control is detected, and controlling a volume of the aroma diffuser when displaying music to the target volume; and determining a target music when an operation of the music selection control is detected, and controlling the aroma diffuser to play the target music.

Among them, the target play mode can be any one of multiple play methods such as random play, single loop play, and sequential play.

When the operation of the volume adjusting control is detected, the target volume can be determined according to the operation of the volume adjusting control. For example, the volume adjusting control is a volume slider. The volume slider includes a slider bar and a slider. When a sliding operation on the slider is detected, the position of the slider on the slider bar is determined, and the target volume is determined according to the position of the slider on the slider bar. It should be noted that before determining the target volume, the correspondence relationship between the position and the volume may be acquired first, and the correspondence relationship at least includes a mapping relationship between the position of the slider on the slider bar and the target volume. Among them, the correspondence relationship between the position and the volume can be acquired from the aroma diffuser control application program, or the correspondence relationship between the position and the volume can be acquired from other devices, which is not limited here.

As shown in FIG. 2D, which is an exemplary image showing updating of the music switch reflection graph, when it is detected that the switch control is turned on, the aroma diffuser is controlled to play music and the music symbol in the music switch reflection graph is rotated; and when it is detected that the switch control is turned off, the aroma diffuser is controlled to stop playing music and the music symbol in the music switch reflection graph is controlled to stop rotating.

It should be noted that the target music can be acquired from the music stored in the mobile terminal, the target music can also be acquired from the music stored in the aroma diffuser, or the target music can be acquired from a third-party music player system, which is not limited herein.

In the embodiments of the present application, the aroma diffuser control page is displayed, and when the operation on the adjusting controls in the aroma diffuser control page is detected, the working mode of the aroma diffuser is adjusted. This process does not need to manually operate the button on the aroma diffuser, thereby being able to more conveniently realize the control of the aroma diffuser. In addition, the updating of the result reflection graph is able to display the adjustment result of the working mode of the aroma diffuser (that is, the control result of the aroma diffuser), thus being convenient for the user to observe the control result of the aroma diffuser more intuitively.

Figure 3:
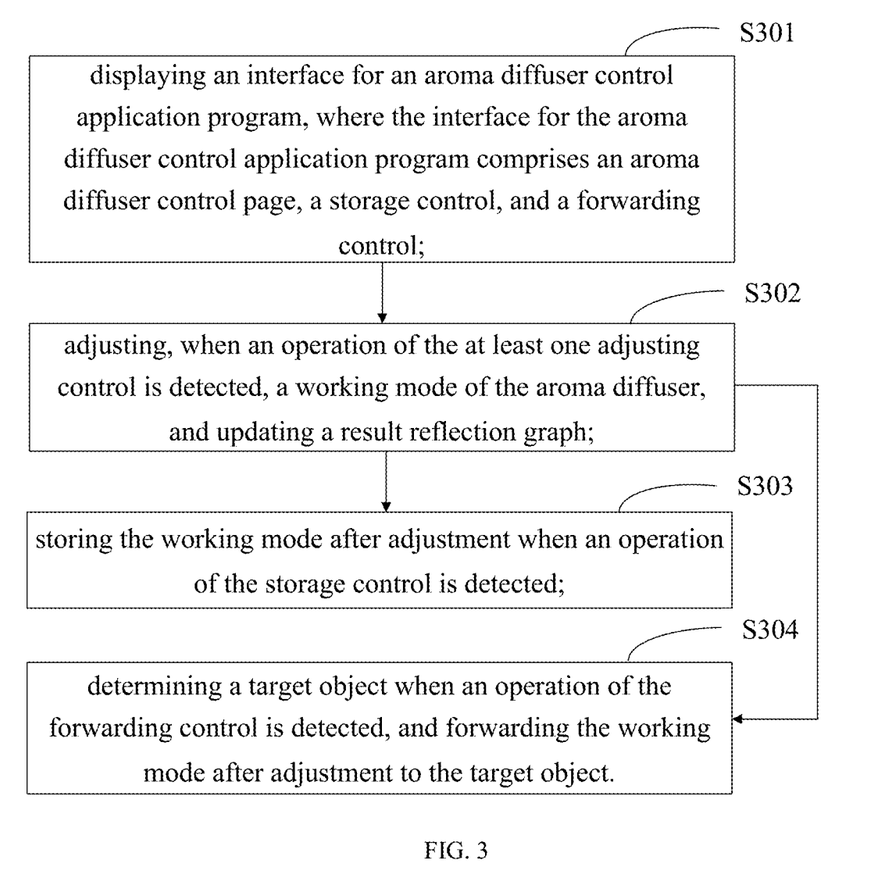
FIG. 3 is a flow chart of implementing a control method for an aroma diffuser provided by a second embodiment of the present application.

FIG. 3 is a flow chart of implementing a control method for an aroma diffuser provided by a second embodiment of the present application. The control method is applied to the mobile terminal. As shown in FIG. 3, the control method may comprise the following steps:

Step 301 of displaying an interface for an aroma diffuser control application program, in which, the interface for the aroma diffuser control application program comprises an aroma diffuser control page, a storage control, and a forwarding control;

In this step, the description related to the interface for the aroma diffuser control application program can be refer to the first embodiment, which will not be repeated herein.

Step 302 of adjusting, when an operation of the at least one adjusting control is detected, a working mode of the aroma diffuser, and updating a result reflection graph;

Such step is the same as step 102, which can be referred to related descriptions of step 102 for specific details, and will not be repeated herein.

Step 303 of storing the working mode after adjustment when an operation of the storage control is detected; and Specifically, when the operation of the storage control is detected, the adjusted working mode can be stored in the aroma diffuser control application program, so that the user can recall the working mode at any time and control the aroma diffuser to work under the working mode without the need of re-adjusting the working mode.

Step 304 of determining a target object when an operation of the forwarding control is detected, and forwarding the working mode after adjustment to the target object.

Specifically, when an operation on the forwarding control is detected, the target object can be determined according to the operation on the forwarding control. The target object includes, but not limited to, friends in social software, other devices, etc., which are not limited here.

On the basis of the first embodiment, this embodiment of the application includes a storage control and a forwarding control, which can store the working mode that the user likes for subsequent recall at any time, and can also share the well set working mode with other friends.

Figure 4:
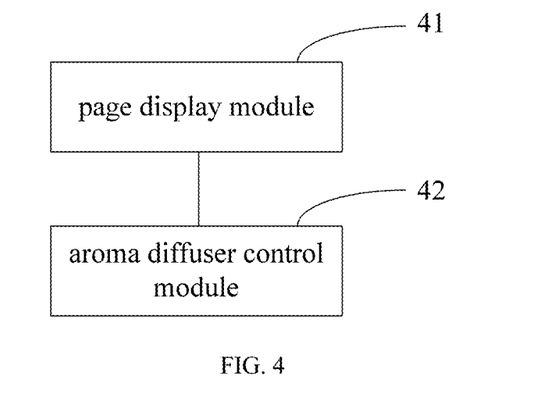
FIG. 4 is a structural diagram of a control device for an aroma diffuser provided by a third embodiment of the present application.

FIG. 4 is a structural diagram of a control device for an aroma diffuser provided by a third embodiment of the present application. For facilitating the description, only those parts related to the embodiment of the present application is illustrated.

The control device comprises:

a page display module 41, configured for displaying an aroma diffuser control page, in which, the aroma diffuser control page comprises a result reflection graph and at least one adjusting control; and an aroma diffuser control module 42, configured for adjusting, when an operation of the at least one adjusting control is detected, a working mode of the aroma diffuser, and updating a result reflection graph, in which, the result reflection graph shows an adjustment result of the working mode.

Optionally, the aroma diffuser is configured to store N essential oils, in which, N is an integer greater than zero. The aroma diffuser control page comprises an essential oil atomization control page, and the essential oil atomization control page comprises: a first adjusting control, and second adjusting controls respectively corresponding to the N essential oils. The result reflection graph comprises an atomization amount reflection graph. The atomization amount reflection graph comprises graph regions corresponding to the N essential oils respectively. The aroma diffuser control module 42 is specifically configured for:

determining a first target atomization amount when an operation of the first adjusting control is detected;

adjusting atomization amounts of the N essential oils to the first target atomization amount, and updating graph regions corresponding to the N essential oils respectively;

determining one or more second target atomization amounts when an operation of one or more of the second adjusting controls is detected; and adjusting atomization amounts of one or more of the N essential oils corresponding to the one or more of the second adjusting controls to the one or more second target atomization amounts, respectively, and updating graph regions corresponding to the one or more types of the N essential oils, respectively.

Optionally, the aroma diffuser control page comprises an atomization duration control page, and the atomization duration control page comprises a duration setting control and a duration adjusting control. The result reflection graph comprises an atomization duration reflection graph. The atomization duration reflection graph comprises a worked region and an un-worked region, in which, the worked region reflects an atomization duration that the aroma diffuser has been subjected, and the un-worked region reflects a remaining atomization duration of the aroma diffuser. The aroma diffuser control module 42 is specifically configured for:

determining a total atomization duration when an operation of the duration setting control is detected;

adjusting an atomization duration of the aroma diffuser to be the total atomization duration, and displaying a countdown of the total atomization duration;

adjusting a proportion of the worked region and a proportion of the un-worked region in the atomization duration reflection graph according to the countdown; and adjusting the remaining atomization duration when an operation of the duration adjusting control is detected, and updating the countdown.

Optionally, the atomization duration control page further comprises a first duration control and a second duration control. The aroma diffuser control module 42 is further configured for:

determining an atomization opening duration of an intermittent cyclic atomization for the aroma diffuser when an operation of the first duration control is detected;

determining an atomization closing duration of the intermittent cyclic atomization for the aroma diffuser when an operation of the second duration control is detected; and controlling the aroma diffuser to perform the intermittent cyclic atomization according to the atomization opening duration, the atomization closing duration, and the total atomization duration, and re-dividing the worked region and the un-worked region in the atomization duration reflection graph.

Optionally, the aroma diffuser is provided with M light sources, in which, M is an integer greater than zero. The aroma diffuser control page comprises a lighting control page, and the lighting control page comprises: a brightness adjusting control, and color adjusting controls corresponding to the M light sources, respectively. The result reflection graph comprises a lighting state reflection graph, and the lighting state reflection graph comprises graph regions corresponding to the M light sources. The step of adjusting, when an operation of the at least one adjusting control is detected, a working mode of the aroma diffuser, and updating a result reflection graph comprises:

determining a target brightness when an operation of the brightness adjusting control is detected;

adjusting brightness of the M light sources, and updating the brightness of graph regions corresponding to the M light sources respectively;

determining one or more target colors when an operation of one or more of the color adjusting controls is detected; and adjusting colors of one or more of the M light sources corresponding to the one or more of the color adjusting controls and colors of one or more of the graph regions corresponding to the one or more of the M light sources to the one or more target colors, respectively.

Optionally, the aroma diffuser control page comprises a music control page. The music control page comprises a switch control, and the result reflection graph comprises a music switch reflection graph. The aroma diffuser control module 42 is specifically configured for:

controlling the aroma diffuser to play music or controlling the aroma diffuser to stop playing music, when an operation of the switch control is detected, and updating the music switch reflection graph;

in which, the music control page further comprises: a play adjusting control, a volume adjusting control, and a music selection control;

determining a target play mode when an operation of the play adjusting control is detected, and controlling the aroma diffuser to play music according to the target play mode;

determining a target volume when an operation of the volume adjusting control is detected, and controlling a volume of the aroma diffuser when displaying music to the target volume; and determining a target music when an operation of the music selection control is detected, and controlling the aroma diffuser to play the target music.

Optionally, the page display module 41 is specifically configured for:

displaying an interface for an aroma diffuser control application program, in which, the interface for the aroma diffuser control application program comprises an aroma diffuser control page, a storage control, and a forwarding control;

The control device further comprises:

a storage module, configured for storing the working mode after adjustment when an operation of the storage control is detected; and a forwarding module, configured for determining a target object when an operation of the forwarding control is detected, and forwarding the working mode after adjustment to the target object.

The control device provided by this embodiment of the present application may apply the methods according to the first embodiment and the second embodiments, these methods may refer to the description of the first embodiment and the second embodiment for details, which would not be repeated herein.

Figure 5:
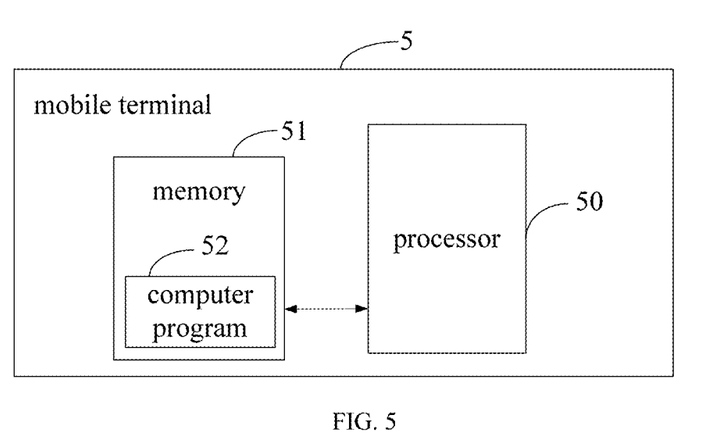
FIG. 5 is a structural diagram of a mobile terminal provided by a fourth embodiment of the present application.

FIG. 5 is a structural diagram of a mobile terminal provided by a fourth embodiment of the present application. As shown in FIG. 5, the mobile terminal 5 of this embodiment comprises: one or more processors 50 (only one shown in the figure), a memory 51, and a computer program 52 stored in the memory 51 and configured to run on the one or more processor 50. The processor is configured to implement the steps as described in the control methods according to the above embodiments when executing the computer program 52.

The mobile terminal 5 may be a mobile device such as a mobile phone or a tablet computer. The mobile terminal may include, but is not limited to, a processor 50 and a memory 51. It will be understood by those skilled in the art that FIG. 5 is only an example of the mobile terminal 5 rather than limiting the mobile terminal 5, and may include more or less components than those illustrated, or combine some components, or different components. For example, the mobile terminal may further include an input/output device, a network access device, a bus, and the like.

The processor 50 may be a central processing unit (CPU), a general purpose processor, a digital signal processor (DSP), an application specific integrated circuit (ASIC), a field-programmable gate array (FPGA), a programmable logic device, a discrete gate or a transistor logic device, a discrete hardware component, etc. The general purpose processor may be a microprocessor or the processor may also be any conventional processor, etc.

The memory 51 may be an internal storage unit of the mobile terminal 5, such as a hard disk or a memory of the mobile terminal 5. The memory 51 may also be an external storage device of the mobile terminal 5, such as a plug-in hard disk, a smart media card (SMC), a secure digital (SD) card, a flash card, etc. provided on the mobile terminal 5. Further, the memory 51 may further include both an internal storage unit and an external storage device of the mobile terminal 5. The memory 51 is used to store the computer program and other programs and data required by the mobile terminal. The memory 51 may also be used to temporarily store data that has been or will be output.

Those skilled in the art may clearly understand that, for the convenience and simplicity of description, only the division of the above functional modules is used as an example. In practical applications, the above function allocation may be accomplished by different functional modules as needed. That is to say, the internal structure of the device is divided into different functional modules to accomplish all or part of the functions described above. Each of the functional modules in some embodiments may be integrated in one processing module, or each of the modules may exist in a single physical manner, or two or more modules may be integrated in one module. The above integrated module may be implemented in the form of hardware, or may be implemented in the form of a software functional module. In addition, the specific names of the various functional modules are merely for the convenience of distinguishing each other and are not intended to limit the protection scope of the present application. For the specific working process of the module in the foregoing device, reference may be made to the corresponding process in the foregoing method embodiment, which will not be described herein again.

In the above embodiments, the description of different embodiments has different focus, and the parts that are not described or recorded in some embodiments may refer to the related descriptions in other embodiments.

It may be appreciated by those skilled in the art that the units and algorithm steps of each example described in combination with the embodiments disclosed herein are capable of being implemented by electronic hardware or a combination of computer software and electronic hardware. Whether these functions are implemented by hardware or software depends on the specific application and design constraints of the technical solutions. Those skilled in the art may use different methods to implement the described functions for each particular application, but such implementation should not be considered to go beyond the scope of the present application.

In the embodiments provided by the present application, it should be understood that the disclosed mobile terminal and method may be implemented in other manners. For example, the mobile terminal embodiments described above is merely exemplary. For example, the division of the modules or units is merely logical function division, and there may be other division manners in actual implementation. For example, multiple units or components may be combined or integrated into another system, or some of the features may be ignored or not implemented. In addition, the mutual coupling or direct coupling or communication connection shown or discussed may be indirect coupling or communication connection through some interfaces, devices or units, and may be in electrical, mechanical, or other forms.

The units described as separate components may or may not be physically separated. The components displayed as units may or may not be physical units. That is to say, the components may be located in one place or may also be distributed to multiple network units. Some or all of the units may be selected according to actual needs to achieve the objectives of the solution in this embodiment.

In addition, each of the function units in different embodiments of the present application may be integrated in one processing unit, or each of the units may exist in a single physical manner, or two or more units may be integrated in one unit. The above integrated module may be implemented in the form of hardware or may be implemented in the form of a software function unit.

If implemented in the form of a software function unit and when sold or used as an independent product, the integrated module/unit may be stored in a computer readable storage medium. Based on this understanding, all or a part of the processes of the present application for implementing the above exemplary method may also be implemented by instructing relevant hardware through a computer program. The computer program may be stored in a computer readable storage medium. The computer program, when being executed by the processor, may implement steps in each of the method embodiments described above. Herein, the computer program includes a computer program code, which may be in the form of a source code, in the form of an object code, in the form of an executable file or in some intermediate form, etc. The computer readable medium may include any entity or device capable of carrying the computer program code, a recording medium, a USB flash drive, a removable disk, a magnetic disk, an optical disk, a computer memory, a read-only memory (ROM), a random access memory (RAM), electrical carrier signals, telecommunications signals, a software distribution medium, etc. It should be noted that the content contained in the computer readable medium may be appropriately increased or decreased according to the requirements of legislation and patent practice in the jurisdiction. For example, in some jurisdictions, according to legislation and patent practice, a computer readable medium excludes electric carrier signals and telecommunication signals.

All or part of the processes implemented in the above-mentioned method embodiments of the present application can be completed by a computer program product. When the computer program product runs on a mobile terminal, the steps in the above method embodiments of the present application can be implemented when the computer program is executed by the mobile terminal.

The foregoing embodiments are merely intended for describing the technical solutions of the present application rather than limiting the present application. Although the present application is described in detail with reference to the foregoing embodiments, it should be understood by those skilled in the art that the technical solutions recorded in each of the foregoing embodiments may still be modified or some of the technical features may be replaced equivalently. These modifications or replacements do not make the essence of the corresponding technical solutions depart from the spirit and scope of the technical solutions of each of the embodiments of the present application, and should be included within the protection scope of the present application.

What is claimed is:

1. A control method for an aroma diffuser, the control method comprising:
   displaying an aroma diffuser control page, wherein the aroma diffuser control page comprises a result reflection graph and at least one adjusting control;
   adjusting, when an operation of the at least one adjusting control is detected, a working mode of the aroma diffuser, and updating the result reflection graph, wherein the result reflection graph shows an adjustment result of the working mode;
   wherein
   the aroma diffuser is configured to store N essential oils, wherein N is an integer greater than zero;
   the aroma diffuser control page comprises an essential oil atomization control page, and the essential oil atomization control page comprises: a first adjusting control, and second adjusting controls respectively corresponding to the N essential oils;
   the result reflection graph comprises an atomization amount reflection graph;
   the atomization amount reflection graph comprises graph regions corresponding to the N essential oils respectively; and
   the step of adjusting, when an operation of the at least one adjusting control is detected, the working mode of the aroma diffuser, and updating the result reflection graph comprises:
      determining a first target atomization amount when an operation of the first adjusting control is detected;
      adjusting atomization amounts of the N essential oils to the first target atomization amount, and updating graph regions corresponding to the N essential oils respectively;
      determining one or more second target atomization amounts when an operation of one or more of the second adjusting controls is detected; and
      adjusting atomization amounts of one or more of the N essential oils corresponding to the one or more of the second adjusting controls to the one or more second target atomization amounts, respectively, and updating graph regions corresponding to the one or more types of the N essential oils, respectively.

2. The control method of claim 1, wherein
the aroma diffuser control page comprises an atomization duration control page, and the atomization duration control page comprises a duration setting control and a duration adjusting control;
the result reflection graph comprises an atomization duration reflection graph;
the atomization duration reflection graph comprises a worked region and an un-worked region, wherein the worked region reflects an atomization duration that the aroma diffuser has been subjected, and the un-worked region reflects a remaining atomization duration of the aroma diffuser;
the step of adjusting, when an operation of the at least one adjusting control is detected, the working mode of the aroma diffuser, and updating the result reflection graph comprises:
   determining a total atomization duration when an operation of the duration setting control is detected;
   adjusting an atomization duration of the aroma diffuser to be the total atomization duration, and displaying a countdown of the total atomization duration;
   adjusting a proportion of the worked region and a proportion of the un-worked region in the atomization duration reflection graph according to the countdown; and
   adjusting the remaining atomization duration when an operation of the duration adjusting control is detected, and updating the countdown.

3. The control method of claim 2, wherein
the atomization duration control page further comprises a first duration control and a second duration control; and
the step of adjusting, when an operation of the at least one adjusting control is detected, the working mode of the aroma diffuser, and updating the result reflection graph further comprises:

determining an atomization opening duration of an intermittent cyclic atomization for the aroma diffuser when an operation of the first duration control is detected;

determining an atomization closing duration of the intermittent cyclic atomization for the aroma diffuser when an operation of the second duration control is detected; and controlling the aroma diffuser to perform the intermittent cyclic atomization according to the atomization opening duration, the atomization closing duration, and the total atomization duration, and re-dividing the worked region and the un-worked region in the atomization duration reflection graph.

4. The control method according to claim 3, wherein the step of displaying the aroma diffuser control page comprises:

displaying an interface for an aroma diffuser control application program, wherein the interface for the aroma diffuser control application program comprises an aroma diffuser control page, a storage control, and a forwarding control;

the control method further comprises the following steps, after the step of adjusting the working mode of the aroma diffuser:

storing the working mode after adjustment when an operation of the storage control is detected; and determining a target object when an operation of the forwarding control is detected, and forwarding the working mode after adjustment to the target object.

5. The control method according to claim 2, wherein the step of displaying the aroma diffuser control page comprises:

displaying an interface for an aroma diffuser control application program, wherein the interface for the aroma diffuser control application program comprises an aroma diffuser control page, a storage control, and a forwarding control;

the control method further comprises the following steps, after the step of adjusting the working mode of the aroma diffuser:

storing the working mode after adjustment when an operation of the storage control is detected; and determining a target object when an operation of the forwarding control is detected, and forwarding the working mode after adjustment to the target object.

6. The control method of claim 1, wherein the aroma diffuser is provided with M light sources, wherein M is an integer greater than zero;

the aroma diffuser control page comprises a lighting control page, and the lighting control page comprises: a brightness adjusting control, and color adjusting controls corresponding to the M light sources, respectively;

the result reflection graph comprises a lighting state reflection graph, and the lighting state reflection graph comprises graph regions corresponding to the M light sources; and the step of adjusting, when an operation of the at least one adjusting control is detected, the working mode of the aroma diffuser, and updating the result reflection graph comprises:

determining a target brightness when an operation of the brightness adjusting control is detected;

adjusting brightness of the M light sources, and updating the brightness of graph regions corresponding to the M light sources respectively;

determining one or more target colors when an operation of one or more of the color adjusting controls is detected; and adjusting colors of one or more of the M light sources corresponding to the one or more of the color adjusting controls and colors of one or more of the graph regions corresponding to the one or more of the M light sources to the one or more target colors, respectively.

7. The control method according to claim 6, wherein the step of displaying the aroma diffuser control page comprises:

displaying an interface for an aroma diffuser control application program, wherein the interface for the aroma diffuser control application program comprises an aroma diffuser control page, a storage control, and a forwarding control;

the control method further comprises the following steps, after the step of adjusting the working mode of the aroma diffuser:

storing the working mode after adjustment when an operation of the storage control is detected; and determining a target object when an operation of the forwarding control is detected, and forwarding the working mode after adjustment to the target object.

8. The control method of claim 1, wherein the aroma diffuser control page comprises a music control page; and the music control page comprises a switch control, and the result reflection graph comprises a music switch reflection graph; and the step of adjusting, when an operation of the at least one adjusting control is detected, the working mode of the aroma diffuser, and updating the result reflection graph comprises:

controlling the aroma diffuser to play music or controlling the aroma diffuser to stop playing music, when an operation of the switch control is detected, and updating the music switch reflection graph; wherein, the music control page further comprises: a play adjusting control, a volume adjusting control, and a music selection control;

determining a target play mode when an operation of the play adjusting control is detected, and controlling the aroma diffuser to play music according to the target play mode;

determining a target volume when an operation of the volume adjusting control is detected, and controlling a volume of the aroma diffuser when displaying music to the target volume; and determining a target music when an operation of the music selection control is detected, and controlling the aroma diffuser to play the target music.

9. The control method according to claim 8, wherein the step of displaying the aroma diffuser control page comprises:

displaying an interface for an aroma diffuser control application program, wherein the interface for the aroma diffuser control application program comprises an aroma diffuser control page, a storage control, and a forwarding control;

the control method further comprises the following steps, after the step of adjusting the working mode of the aroma diffuser:

storing the working mode after adjustment when an operation of the storage control is detected; and determining a target object when an operation of the forwarding control is detected, and forwarding the working mode after adjustment to the target object.

10. The control method according to claim 1, wherein the step of displaying the aroma diffuser control page comprises:

displaying an interface for an aroma diffuser control application program, wherein the interface for the aroma diffuser control application program comprises an aroma diffuser control page, a storage control, and a forwarding control;

the control method further comprises the following steps, after the step of adjusting the working mode of the aroma diffuser:

storing the working mode after adjustment when an operation of the storage control is detected; and determining a target object when an operation of the forwarding control is detected, and forwarding the working mode after adjustment to the target object.

11. A control device for an aroma diffuser, the control device comprising:

a processor configured to control the modules comprising:

a page display module, configured for displaying an aroma diffuser control page, wherein the aroma diffuser control page comprises a result reflection graph and at least one adjusting control; and an aroma diffuser control module, configured for adjusting, when an operation of the at least one adjusting control is detected, a working mode of the aroma diffuser, and updating the result reflection graph, wherein the result reflection graph shows an adjustment result of the working mode;

wherein the aroma diffuser is configured to store N essential oils, wherein N is an integer greater than zero;

the aroma diffuser control page comprises an essential oil atomization control page, and the essential oil atomization control page comprises: a first adjusting control, and second adjusting controls respectively corresponding to the N essential oils;

the result reflection graph comprises an atomization amount reflection graph;

the atomization amount reflection graph comprises graph regions corresponding to the N essential oils respectively; and the step of adjusting, when an operation of the at least one adjusting control is detected, the working mode of the aroma diffuser, and updating the result reflection graph comprises:

determining a first target atomization amount when an operation of the first adjusting control is detected;

adjusting atomization amounts of the N essential oils to the first target atomization amount, and updating graph regions corresponding to the N essential oils respectively;

determining one or more second target atomization amounts when an operation of one or more of the second adjusting controls is detected; and adjusting atomization amounts of one or more of the N essential oils corresponding to the one or more of the second adjusting controls to the one or more second target atomization amounts, respectively, and updating graph regions corresponding to the one or more types of the N essential oils, respectively.

12. A mobile terminal, comprising: a memory, a processor, and a computer program stored in the memory and running on the processor, wherein the processor is configured for realizing the steps of the control method according to claim 1 when executing the computer program.

* * * * *